US012788973B2

(12) United States Patent
Williams et al.

(10) Patent No.: US 12,788,973 B2
(45) Date of Patent: Nov. 10, 2026

(54) NEUROMODULATION TO MODULATE GLYMPHATIC CLEARANCE

(71) Applicants: Wisconsin Alumni Research Foundation, Madison, WI (US); Mayo Foundation for Medical Education and Research, Rochester, MN (US)

(72) Inventors: Justin Williams, Madison, WI (US); Kip Ludwig, Rochester, MN (US); Erika Ross, San Mateo, CA (US)

(73) Assignees: Wisconsin Alumni Research Foundation, Madison, WI (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/672,957

(22) Filed: May 23, 2024

(65) Prior Publication Data

US 2024/0307681 A1 Sep. 19, 2024

Related U.S. Application Data

(60) Continuation of application No. 17/884,784, filed on Aug. 10, 2022, now Pat. No. 12,005,251, which is a division of application No. 16/326,824, filed as application No. PCT/US2017/048683 on Aug. 25, 2017, now Pat. No. 11,426,577.

(Continued)

(51) Int. Cl.

| | |
|---|---|
| ***A61M 60/135*** | (2021.01) |
| ***A61N 1/04*** | (2006.01) |
| ***A61N 1/05*** | (2006.01) |
| ***A61N 1/36*** | (2006.01) |
| ***A61N 1/375*** | (2006.01) |

(52) U.S. Cl.

CPC ........... *A61N 1/056* (2013.01); *A61N 1/0456* (2013.01); *A61N 1/0476* (2013.01); *A61N 1/0484* (2013.01); *A61N 1/0492* (2013.01); *A61N 1/0536* (2013.01); *A61N 1/0551* (2013.01); *A61N 1/36025* (2013.01); *A61N 1/36034* (2017.08); *A61N 1/36053* (2013.01); *A61N 1/36067* (2013.01); *A61N 1/36082* (2013.01); *A61N 1/36103* (2013.01); *A61N 1/36132* (2013.01); *A61N 1/36146* (2013.01); *A61N 1/36175* (2013.01); *A61N 1/37516* (2017.08)

(58) Field of Classification Search

CPC .. A61N 1/3751; A61N 1/3603; A61N 1/0456; A61N 1/056

See application file for complete search history.

(56) References Cited

U.S. PATENT DOCUMENTS 7,013,177 B1 * 3/2006 Whitehurst ........ A61N 1/36071 607/46
2004/0220644 A1 * 11/2004 Shalev ............... A61N 1/36082 607/45

(Continued)

*Primary Examiner* — Carl H Layno
*Assistant Examiner* — Jennifer L Ghand
(74) *Attorney, Agent, or Firm* — Boyle Fredrickson, S.C.

(57) ABSTRACT

The present invention provides materials and methods for using electrical stimulation to treat a mammal having a proteinopathy (e.g., neurodegenerative diseases) or at risk of developing a proteinopathy are provided. For example, the present invention provides materials and methods for modulating glymphatic clearance (e.g., enhancing glymphatic clearance) of pathogenic proteins.

15 Claims, 4 Drawing Sheets

Related U.S. Application Data

(60) Provisional application No. 62/379,941, filed on Aug. 26, 2016.

(56) References Cited

U.S. PATENT DOCUMENTS

| | | | | |
|---|---|---|---|---|
| 2005/0159790 | A1* | 7/2005 | Shalev | A61M 5/1723 607/45 |
| 2008/0071150 | A1* | 3/2008 | Miesel | G16H 20/30 600/509 |
| 2011/0071457 | A1* | 3/2011 | Raman | A61M 27/006 604/9 |
| 2013/0066392 | A1* | 3/2013 | Simon | A61N 2/006 607/45 |
| 2015/0018634 | A1* | 1/2015 | Zhu | A61N 1/36135 600/301 |
| 2018/0117364 | A1* | 5/2018 | Jordan | A61N 7/00 |
| 2019/0282807 | A1* | 9/2019 | Tendler | A61N 1/327 |
| 2023/0381509 | A1* | 11/2023 | Ludwig | A61N 1/36025 |

* cited by examiner

NEUROMODULATION TO MODULATE GLYMPHATIC CLEARANCE

CROSS REFERENCE TO RELATED APPLICATIONS

This application is a continuation of U.S. application Ser. No. 17/884,784, filed Aug. 10, 2022, issued as U.S. Pat. No. 12,005,251, which is a divisional of U.S. application Ser. No. 16/326,824, filed Feb. 20, 2019, issued as U.S. Pat. No. 11,426,577, which is the National Stage of International Application No. PCT/US2017/048683, filed Aug. 25, 2017, which claims the benefit of U.S. Provisional Application No. 62/379,941, filed Aug. 26, 2016, each of which is hereby incorporated by reference.

BACKGROUND OF THE INVENTION

1. Technical Field

The present invention relates to materials and methods for using neurostimulation to treat a mammal having a proteinopathy (e.g., neurodegenerative diseases) or at risk of developing a proteinopathy. Specifically, the present invention provides materials and methods for using electrical stimulation for modulating glymphatic clearance (e.g., enhancing glymphatic clearance) of pathogenic proteins in a mammal having a proteinopathy or at risk of developing a proteinopathy.

2. Background Information

The glymphatic system (or glymphatic clearance pathway) is a macroscopic waste clearance system for the vertebrate central nervous system (CNS) utilizing a unique system of perivascular tunnels formed by glial cells to promote efficient elimination of soluble and insoluble proteins and metabolites from the central nervous system (CNS). The pathway provides a para-arterial influx route for cerebrospinal fluid (CSF) to enter the brain parenchyma and a clearance mechanism via convective movement of interstitial fluid (ISF) for extracellular solutes such as misfolded proteins and unwanted metabolites to be removed from the brain.

It has been found that the aggregation of pathogenic proteins β-amyloid, α-synuclein, and C-tau in the brain may cause the deleterious effects of numerous disease and disorders such as traumatic brain injury/chronic traumatic encephalothopy, epilepsy, Alzheimer's disease, and Parkinson's disease. Removal of these pathogenic proteins has been found to have substantial therapeutic benefit, for example, in treating traumatic brain injury/chronic traumatic encephalothopy, epilepsy, Alzheimer's disease, and Parkinson's disease.

SUMMARY OF THE INVENTION

Glymphatic clearance of pathogenic proteins may be enhanced by 1) modulating the interstitial volume directly to increase clearance via convection and 2) changing the interstitial volume between cells to decrease the resistance to glymphatic flow, indirectly increasing glymphatic flow (changing the interstitial volume manipulates the effective distance between neural cell types, reducing the resistance to glymphatic flow between cells). The present invention recognizes that these mechanisms may be enhanced through the neurobiological effects of electrical stimulation in a patient.

The present invention provides materials and methods for using electrical stimulation to treat a mammal having a proteinopathy or at risk of developing a proteinopathy under conditions wherein the severity of the proteinopathy or chance of developing a proteinopathy is reduced. For example, the present invention provides materials and methods for using electrical stimulation to modulate glymphatic clearance (e.g., enhancing glymphatic clearance) of pathogenic proteins. Various electrical stimulation therapies and/or emerging electrical stimulation technologies may be used.

In one embodiment, the present invention features a method of modulating glymphatic clearance in a mammal. The method includes, or consists essentially of, administering electrical stimulation to the mammal under conditions wherein the electrical stimulation is effective to enhance glymphatic clearance of one or more pathogenic proteins from the central nervous system of the mammal. The electrical stimulation to the mammal may be under conditions wherein the electrical stimulation is effective to increase interstitial fluid (ISF)—cerebrospinal fluid (CSF) exchange in the mammal or to draw charged proteins toward venous return.

It is thus a feature of at least one embodiment of the invention to provide continuous electrical stimulation delivery during patient consciousness or unconsciousness without compromising the functions of the sensory nervous system.

The electrical stimulation to the mammal may be under conditions wherein the electrical stimulation is effective to increase CSF production.

It is thus a feature of at least one embodiment of the invention to increase the driving pressure of CSF into the perivascular space (or Virchow-Robin spaces).

The electrical stimulation to the mammal may be under conditions wherein the electrical stimulation is effective to modulate pulsatility of penetrating arterial vessels.

It is thus a feature of at least one embodiment of the invention to increase the pulsation generated by smooth muscle cells along the length of the pial and penetrating arteries to drive paravascular CSF influx.

The electrical stimulation to the mammal may be under conditions wherein the electrical stimulation is effective to increase aquaporin-4 (AQP4) water channel permeability.

It is thus a feature of at least one embodiment of the invention to increase the water movement though AQP4 water channels, increasing the penetration of CSF into ISF.

The electrical stimulation to the mammal may be under conditions wherein the electrical stimulation is effective to decrease the resistance of CSF penetration in the ISF space. The electrical stimulation may be under conditions wherein the electrical stimulation is effective to decrease intracellular fluid volume and/or increase the distance between neuronal/non-neuronal cells.

It is thus a feature of at least one embodiment of the invention to allow for more efficient CSF flow into the Virchow-Robin spaces.

The electrical stimulation to the mammal may be under conditions wherein the electrical stimulation is effective to induce slow wave oscillations in specific brain areas.

It is thus a feature of at least one embodiment of the invention to induce conditions linked to changing interstitial volume during sleep.

Electrical stimulation to the mammal may be administered during sleep. Electrical stimulation to the mammal may be under conditions wherein glymphatic clearance during sleep is enhanced by at least 10%, 15% or 20%.

It is thus a feature of at least one embodiment of the invention to administer stimulation while the patient is unconscious and primed for glymphatic clearance. It is also a feature of at least one embodiment of the invention to allow the patient to function with less sleep by increasing the protein clearance and thus decreasing the negative cognitive consequences of less sleep.

Electrical stimulation to the mammal may be administered to skin sympathetic nerves in feet during sleep.

It is thus a feature of at least one embodiment of the invention to encourage blood flow to the brain and drive clearance during periods of increased interstitial space during sleep, as similarly found during foot impact during walking or running.

Several nerves may be stimulated simultaneously to modulate sympathetic and parasympathetic arms of the autonomic nervous system in tandem.

It is thus a feature of at least one embodiment of the invention to drive clearance with synchronous stimulation.

The method may include determining whether or not the severity of a symptom is reduced using at least one of the following methods: computerized topography (CT) scan, diffuse optical imaging (DOI), event-related optical signal (EROS), magnetic resonance imaging (MRI), functional magnetic resonance imaging (fMRI), magnetoencephalography (MEG), positron emission tomography (PET), single-photon emission computed tomography (SPECT), cranial ultrasound, learning tests and memory tests, motor function testing, sensory function testing, biopsy, CSF testing, blood testing and genetic testing.

It is thus a feature of at least one embodiment of the invention to train the patient to self-administer the electrical stimulation to maximize response. Feedback may be in real time with feedback mechanisms delivered to the client.

The electrical stimulation to the mammal may be under conditions wherein the electrical stimulation to the mammal includes an implanted intravenous electrode and the electrical stimulation is effective to attract proteins to the implanted electrode subjected to the electrical stimulation. The implanted electrode may be placed within the sagittal sinus vein.

It is thus a feature of at least one embodiment of the invention to draw proteins to a waste removal location.

The implanted electrode may be inserted into a vein by a stent having an insulated interior surrounded by external electrodes.

It is thus a feature of at least one embodiment of the invention to prevent protein build up inhibiting blood flow through the vein.

Electrical stimulation may be delivered to the implanted electrode in biphasic pulses.

It is thus a feature of at least one embodiment of the invention to safely generate a charge bias in the electrodes attracting the charged proteins toward the electrodes.

The electrical stimulation may be invasive or noninvasive electrical stimulation such as vagus nerve stimulation, carotid sinus nerve stimulation, transcranial direct current stimulation, transcranial magnetic stimulation, or deep brain stimulation.

It is thus a feature of at least one embodiment of the invention to stimulate multiple areas of the brain simultaneously (i.e., the entire brain cortex including deep brain areas). It is thus a feature of at least one embodiment of the invention to stimulate multiple areas of the brain simultaneously using a single input pathway connected to said areas such as the trigeminal nerve.

In one embodiment, the present invention features a method for treating a human having a proteinopathy. The method includes, or consists essentially of placing an electrode over a nerve of the human having the proteinopathy and administering electrical stimulation to the electrode under conditions wherein electrical current is delivered to the nerve and the proteinopathy is reduced.

It is thus a feature of at least one embodiment of the invention to allow the electrical generator to be wearable by the patient and used by the patient throughout the day without direct visual medical supervision.

Electrical stimulation to the mammal may be administering electrical current to the trigeminal nerve.

It is thus a feature of at least one embodiment of the invention to stimulate nerves non-invasively through the patient's skin.

In one embodiment, the present invention features a method for treating a human having a proteinopathy. The method includes, or consists essentially of implanting an electrode within a blood vessel of the human having the proteinopathy and administering electrical stimulation to the electrode under conditions wherein proteins are drawn to the electrode and the proteinopathy is reduced.

It is thus a feature of at least one embodiment of the invention to utilize the polarization of the proteins to draw proteins to a desired location within the body for waste removal.

These particular objects and advantages may apply to only some embodiments falling within the claims and thus do not define the scope of the invention.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENT

Figure 1A:
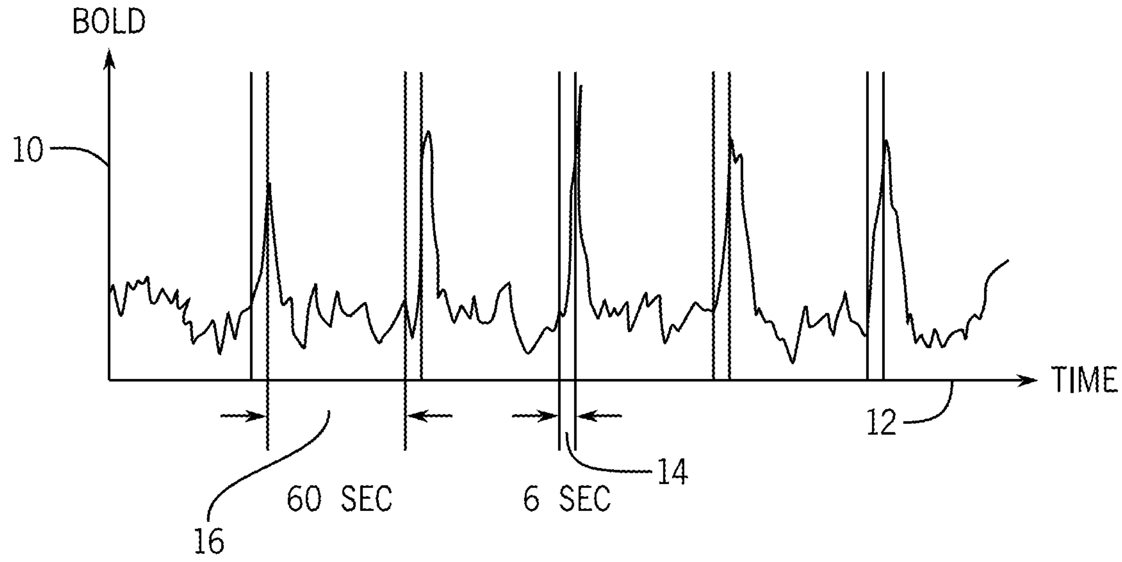
FIGS. 1A and 1B are charts showing blood oxygen level-dependent (BOLD) effects during vagus nerve stimulation in swine.

The glymphatic system is the body's waste clearance pathway for the central nervous system (CNS). The term "glymphatic system" was coined based on its similar functions to the lymphatic system and its reliance on glial cells, which surround neurons in the brain and provide support and protection for the brain's neurons. One type of glial cell are astrocytes that ensheathe the brain's blood vessel endothelial cells and are responsible for providing biochemical support for the endothelial cells that form the blood-brain barrier, provide nutrients to the nervous tissue, maintain extracellular ion balance, and repair the brain and spinal cord following traumatic injuries.

The glymphatic system is responsible for the exchange of cerebral spinal fluid (CSF) and interstitial fluid (ISF) that is driven by arterial pulsation, respiration, slow vasomotion, and CSF pressure gradients. In particular, aquaporin-4 (AQP4) water channels found in the astrocytic endfeet assist with the large water fluxes into and out of the brain or spinal cord as part of the CSF-ISF exchange.

At the CSF-ISF exchange, CSF is formed in the choroid plexuses of the ventricles of the brain and driven into the brain parenchyma causing convective ISF fluid fluxes that transport waste products such as misfolded proteins and unwanted metabolites into the ISF. Interstitial proteins are cleared into the blood through the blood-brain barrier or directly into the CSF via ISF bulk flow that enter the perivascular space and travel along perivascular drainage pathways to move the ISF toward leptomeningeal arteries at the surface of the brain and, ultimately, to cervical lymph nodes which remove the potentially hazardous misfolded proteins and unwanted metabolites from the brain. This exchange is modulated by arterial pulsatility and is enhanced during sleep when the interstitial volume is increased to improve folded proteins, waste product, and excess fluid clearance.

Increasing CSF-ISF exchange enhances clearance of neurotoxic metabolic products, misfolded soluble and insoluble proteins, reactive metabolites, etc., and may be facilitated by actions at several points in the glymphatic system. These actions may include at least one of 1) increasing CSF production to create a driving pressure to increase flow of CSF into the Virchrow-Robin spaces, 2) dilating and/or modulating pulsitility of the penetrating arterial vessels, 3) increasing the permeability of AQP4 water channels expressed in astrocytic endfeet that ensheath the brain vasculature, 4) decreasing intracellular fluid volume therefore decreasing the resistance to CSF penetration in the ISF space, for example by decreasing local norepinephrine, and/or 5) inducing slow wave oscillations in specific brain areas that are the hallmark of rapid eye movement (REM) sleep. 6) Intravenous electrodes may also be used to draw proteins towards venous return. These actions will be further described in detail below.

A method for treating a mammal (e.g., a human) having a proteinopathy described herein may include identifying the mammal as having a proteinopathy (e.g., a neurodegenerative disease) or as being at risk of developing a proteinopathy (e.g., a neurodegenerative disease). Any appropriate method may be used to identify a mammal having a proteinopathy or as being at risk for developing a proteinopathy. For example, neuroimaging techniques (e.g., computerized topography (CT) scan, diffuse optical imaging (DOI), event-related optical signal (EROS), magnetic resonance imaging (MRI), functional magnetic resonance imaging (fMRI), magnetoencephalography (MEG), positron emission tomography (PET), single-photon emission computed tomography (SPECT), and cranial ultrasound), cognitive function testing (e.g., learning tests and memory tests), motor function testing, sensory function testing, biopsy, CSF testing, blood testing and/or genetic testing may be used to identify a human or other mammal having a proteinopathy. Mammals who are at risk of developing a proteinopathy may be identified by genetic screening or through concomitant risk factors (hypertension, sleep apnea, etc.).

Any type of mammal having a proteinopathy (e.g., a neurodegenerative disease) or at risk for developing a proteinopathy (e.g., a neurodegenerative disease) may be treated as described herein. For example, humans and other primates such as monkeys having aggregates of proteins may be treated with electrical stimulation. In some cases, dogs, cats, horses, cows, pigs, sheep, rabbits, mice, and rats may be treated with electrical stimulation, as described herein.

When treating a proteinopathy or risk of proteinopathy in a patient as described herein, the proteinopathy may be a proteinopathy associated with aggregation, misfolding, and/or neurotoxic accumulation of any pathogenic protein in the CNS. Examples of proteinopathy include, for example, traumatic brain injury (TBI), epilepsy, Alzheimer's disease (AD), Parkinson's disease (PD), chronic traumatic encephalopathy (CTE), amyotrophic lateral sclerosis (ALS), Huntington's disease, Lewy Body Disease (LBD), Batten disease, frontotemporal dementia (FTD), inclusion body myopathy (IBM), and Paget's disease of bone (PDB). A pathogenic protein whose aggregation and/or misfolding is associated with a proteinopathy may be a wild type protein or a mutated protein. A pathogenic protein whose aggregation, misfolding, and/or neurotoxic accumulation is associated with a proteinopathy may be a soluble protein or an insoluble protein. Examples of pathogenic proteins whose aggregation, misfolding, and/or neurotoxic accumulation is associated with a proteinopathy include, without limitation, amyloid β (AB), apolipoprotein E (APOE), α-synuclein (α-syn), DJ-1, LRRK2, PINKI/PARKIN, tau, C-tau), Huntingtin protein, superoxide dismutase 1 (SOD1), TAR DNA-binding protein 43 (TDP-43), FUS, progranulin, and SCNIA. In some cases, a pathogenic protein whose aggregation, misfolding, and/or neurotoxic accumulation is associated with a proteinopathy may be a mutated protein (e.g., mutant Huntingtin protein (mHtt), SOD1 mutant G93A). In some embodiments, the proteinopathy treated as described herein may be amyotrophic lateral sclerosis (ALS) associated with aggregation of wild type and/or mutant forms of SOD1, TDP-43, and/or FUS. In some embodiments, the proteinopathy treated as described herein may be Alzheimer's disease associated with aggregation of misfolded AB and/or associated with aggregation of tau. In some embodiments, the proteinopathy treated as described herein may be Parkinson's disease associated with aggregation of α-syn. In some embodiments, the proteinopathy treated as described herein may be Huntington's disease associated with aggregation of mHtt.

The materials and methods provided herein may be used to reduce the severity of a proteinopathy (e.g., a neurodegenerative disease). The severity of a neurodegenerative disease may be evaluated by examining symptoms of neurodegenerative diseases such as, without limitation, loss of neurons, cognitive decline, motor impairments, sensory loss, memory loss, and/or memory dysfunction. The materials and methods provided herein may also be used to as a prophylactic treatment in individuals predisposed to a proteinopathy.

The present invention may also be used to improve the condition of mammals with sleep deprivation by using electrical stimulation as a sleep enhancement, improving the clearance of proteins by at least 10%, 15% or 20% in a patient during sleep, and thus, minimizing the amount of sleep needed by the mammal before the effects of cognitive decline are seen in the patient.

Once identified as having a proteinopathy (e.g., a neurodegenerative disease) or as being at risk for developing a proteinopathy, the mammal may be administered or instructed to self-administer electrical stimulation.

Methods for modulating glymphatic clearance described herein may include any appropriate form of electrical stimulation. Examples of electrical stimulation that may be used as described herein include, without limitation, peripheral nerve stimulation (e.g., vagus nerve stimulation and/or carotid sinus nerve stimulation), transcranial direct current stimulation (tDCS), deep brain stimulation (DBS), cortical stimulation, spinal cord stimulation (SCS), transcranial magnetic stimulation (TMS), focused ultrasound, infrared stimulation, direct simulation of nerves using a light source, genetic modification to enhance sensitivity and specificity of the nerve to stimulation with a light source (optogenetics), and use of intravascular electrodes.

The electrical stimulation may be used to electrically stimulate any appropriate portion of the nervous system including, without limitation, the CNS (e.g., brain, spinal cord, retina, optic nerve, olfactory nerves, olfactory epithelium, ventricles, and choroid plexus), the peripheral nervous system (PNS) (e.g., vagus nerves, carotid sinus nerves, aortic nerves, accessory nerves, and spinal nerves (e.g., cervical, brachial, and lumbosacral)), sympathetic nervous system, and parasympathetic nervous system. The present invention also provides skin sympathetic nerve stimulation in feet during sleep to encourage blood flow to the brain (pressure waves are sent through the arteries to modify and increase the supply of blood to the brain) and drive glymphatic clearance during periods of increased interstitial space.

Figure 4:
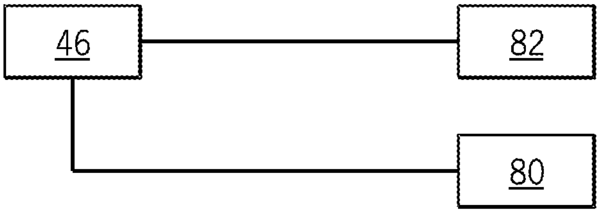
FIG. 4 is a block diagram of the elements of a closed loop control system.

The electrical stimulation may be used to electrically stimulate one or more nerves. In some cases, where the electrical stimulation electrically stimulates more than one nerve, the nerves may be located independently or in a ganglion. Several nerves may be stimulated simultaneously to modulate sympathetic and parasympathetic arms of the autonomic nervous system in tandem to drive clearance with synchronous stimulation. In some cases, the electrical stimulation may be used in a closed-loop fashion by way of combining any form of electrical stimulation mentioned with a sensing modality that may include electrophysiological and/or CSF flow rate measurement. Referring to FIG. 4, such closed loop control of electrical stimulation through CSF flow measurement may include a sensor 80 for measuring CSF flow, a stimulation device 82 to stimulate the cranial nerve and/or the cortical region of the brain and a pulse generator 46 to implement a closed-loop modulation of the stimulating signal based on the CSF flow measurement. Additionally, non-invasive measurements of autonomic nerve activity may be performed, including, blood pressure, galvanic skin response, heart rate, and respiration variability.

In one embodiment, the electrical stimulation may be used to deliver an electrical current to target the CNS. Electrical stimulation of these target areas may be facilitated by any electrical current delivery method, for example, tDCS of the brain, TMS of the brain, ultrasound stimulation of the brain, DBS, epidural/subdural and subcortical electrode stimulation of the brain, epidural electrodes to stimulate the autonomic system at the spinal cord, and transcutaneous SCS of the autonomic nerves at the spinal cord.

In one embodiment, the electrical stimulation may be used to deliver an electrical current to target a division of the PNS such as the autonomic nerves and may be directed specifically to, for example, the auricular vagus nerve, trigeminal nerve, facial nerve, lingual nerve, cervical vagus nerve, carotid sinus nerve, aortic depressor nerve, baroreceptors on carotid sinus bulb, and/or superior cervical ganglia. Stimulation of these target nerves may be facilitated by any commercially available electrical current delivery device, for example, CVRx (minimally invasive electrode for carotid baroreceptors), Neurosigma (non-invasive stimulation of the trigeminal nerve), LivaNova (implantable bipolar cuff to stimulate cervical vagus), and Gammacore (non-invasive stimulation of the cervical vagus).

In one embodiment, the electrical stimulation may be used to deliver an electrical current to electrodes implanted intravascularly in a patient by injecting the patient using a needle delivery system. Implantation of electrodes may be facilitated by any commercially available electrode implantation and monitoring/communication system, for example, StimWave System (for spinal cord stimulation) and Alfred Mann BION stimulator.

Effective levels of electrical stimulation may vary depending on the severity of the proteinopathy (e.g., a neurodegenerative disease), type of stimulation, the age and general health condition of the subject, excipient usage, the possibility of co-usage with other therapeutic treatments such as use of other agents, and the judgment of the treating physician.

An effective electrical stimulation voltage may be any voltage that reduces the severity of a proteinopathy (e.g., a neurodegenerative disease) being treated without producing significant toxicity to the mammal. In some cases, an effective PNS electrical stimulation voltage (V) may be from about 0.1 V to about 20 V (e.g., about 0.5 V to about 18 V, about 1 V to about 15 V, about 2 V to about 12 V, about 3 V to about 10 V, or about 4 V to about 7 V). For example, an effective electrical stimulation voltage may be about 5 V. In some cases, an effective PNS electrical stimulation current (Amps) may be from about 0.1 mA to about 206 mA (e.g., about 0.5 mA to about 150 mA, about 1 mA to about 125 mA, about 1.5 mA to about 100 mA, about 2 mA to about 75 mA, about 2.5 mA to about 50 mA, or about 3.0 mA to about 25 mA). For example, an effective electrical stimulation current may be about 3.5 mA. The effective electrical stimulation voltage may remain constant or may be adjusted as a sliding scale or be variable depending on the mammal's response to treatment. Various factors may influence the actual effective electrical stimulation voltage used for a particular application. For example, the frequency of administration, duration of treatment, use of multiple treatment agents, type of neurostimulation, and severity of the proteinopathy (e.g., a neurodegenerative disease) may require an increase or decrease in the actual effective electrical stimulation voltage administered.

Electrical stimulation may be administered in a continuous delivery or a pulsed delivery. In some cases, a PNS pulsed electrical stimulation may have a pulse rate of about 1 Hz to about 200 Hz (e.g., about 2 Hz to about 150 Hz, about 5 Hz to about 100 Hz, about 8 Hz to about 75 Hz, about 10 Hz to about 50 Hz, or about 15 Hz to about 25 Hz). For example, a pulsed electrical stimulation may have a pulse rate of about 20 Hz. A pulsed electrical stimulation may maintain a constant pulse rate or a pulse rate may be adjusted as a sliding scale or variable pulse rates depending on the mammal's response to treatment. Various factors may influence the actual pulse rate used for a particular application. For example, the frequency of administration, duration of treatment, use of multiple treatment agents, type of electrical stimulation, and severity of the proteinopathy (e.g., a neurodegenerative disease) may require an increase or decrease in the actual electrical stimulation pulse rate administered.

The frequency of administration may be any frequency that reduces the severity of a proteinopathy (e.g., a neurodegenerative disease) to be treated without producing significant toxicity to the mammal. For example, the frequency of administration may be from about once a week to about three times a day, from about twice a month to about six times a day, or from about twice a week to about once a day. The frequency of administration may remain constant or may be variable during the duration of treatment. A course of treatment with electrical stimulation may include rest periods. For example, electrical stimulation may be administered daily over a two-week period followed by a two-week rest period, and such a regimen may be repeated multiple times. As with the effective electrical stimulation voltage and electrical stimulation pulse rate, various factors may influence the actual frequency of administration used for a particular application. For example, the effective amount, duration of treatment, use of multiple treatment agents, route of administration, and severity of the proteinopathy (e.g., a neurodegenerative disease) may require an increase or decrease in administration frequency.

An effective duration for administering electrical stimulation may be any duration that reduces the severity of a proteinopathy (e.g., a neurodegenerative disease) to be treated without producing significant toxicity to the mammal. For example, the effective duration may vary from several days to several weeks, months, or years. In some cases, the effective duration for the treatment of a proteinopathy may range in duration from about one month to about 10 years. Multiple factors may influence the actual effective duration used for a particular treatment. For example, an effective duration may vary with the frequency of administration, effective amount, use of multiple treatment agents, route of administration, and severity of the proteinopathy being treated.

In some cases, electrical stimulation may be administered to a mammal having a proteinopathy (e.g., a neurodegenerative disease) or at risk of developing a proteinopathy (e.g., a neurodegenerative disease) as a combination therapy with one or more additional agents/therapies used to treat a proteinopathy (e.g., a neurodegenerative disease) and/or one or more additional agents/therapies used to increase ISF-CSF exchange. For example, a combination therapy used to treat a mammal having a proteinopathy (e.g., a neurodegenerative disease) may include administering to the mammal (e.g., a human) electrical stimulation and one or more treatments such as medication (e.g., latrepirdine, riluzole, donepezil, galantamine, memantine, rivastigmine, exelon, and/or L-dopa), protein therapy (e.g., protein degradation therapy), and/or immunotherapy (e.g., active vaccination and/or passive vaccination). In embodiments where electrical stimulation is administered in combination with one or more additional agents used to treat a proteinopathy (e.g., a neurodegenerative disease), the one or more additional agents may be administered at the same time or independently. For example, the electrical stimulation may be administered first, and the one or more additional agents administered second, or vice versa. In some embodiments, focused ultrasound may be used to break-up aggregations of proteins into smaller aggregates/individual proteins, to increase mobility in conjunction with electrical stimulation to enhance clearance.

The materials and methods provided herein may be used for using electrical stimulation to treat a mammal having a proteinopathy (e.g., a disease or disorder, such as a neurodegenerative disease, associated with protein aggregation, protein misfolding, and/or neurotoxic protein accumulation in the CNS). In some cases, electrical stimulation may be used to reduce the severity of a proteinopathy. In some cases, electrical stimulation may be used to modulate glymphatic clearance (e.g., enhancing glymphatic clearance) of pathogenic proteins from the CNS. In some cases, electrical stimulation may be used to enhance clearance of one or more pathogenic proteins (e.g., aggregated pathogenic proteins) associated with a proteinopathy from the CNS. In some cases, electrical stimulation may be used to increase the volume of ISF and/or increase the effective distance between neurons thereby limiting ephaptic coupling implicated in abnormal circuit behaviors which behaviors that are the hallmark of multiple disorders of the nervous system (for example, epilepsy and Parkinson's disease). In some cases, electrical stimulation may be used to increase mitochondrial biogenesis in the CNS to 1) improve degradation of misfolded proteins, 2) clearance of misfolded proteins from the CNS, and 3) decrease the pro-inflammatory protein expression (i.e. TNF-alpha, and, associated with expression of misfolded proteins.

In some cases, electrical stimulation may be used to increase interstitial fluid (ISF)-cerebrospinal fluid (CSF) exchange. ISF-CSF exchange may be facilitated by, for example, 1) increasing CSF production, 2) modulating pulsatility of the penetrating arterial vessels, 3) increasing the permeability of AQP4 water channels, 4) decreasing intracellular fluid volume, and 5) inducing slow wave oscillations in specific brain areas (e.g., areas associated with REM sleep). For example, ISF-CSF exchange may be increased using sympathetic inhibition (e.g., sympathectomy), modulating adenosine and/or epinephrine/norepinephrine release, increasing interstitial space and/or volume, activating locus coeruleus, activating choroid plexus ependymal cells, and/or activating astrocytes and/or AQP4 channels at the neurovascular junction. Electrical stimulation may also be used to 6) directly attract proteins to an intravenous electrode via application of a stimulus waveform. Each of the possible conditions facilitating glymphatic clearance is described in more detail below.

1. Increasing CSF Production to Create a Driving Pressure to Increase Flow of CSF into the Virchow/Robin Spaces, Thereby Enhancing Glymphatic Clearance Glymphatic transport of the CSF along the periarterial spaces followed by convective flow through the brain parenchyma and exit of ISF along the perivenous space to the cervical lymph system is driven by multiple mechanisms. One mechanism is the constant production of CSF by the choroid plexus providing a driving force to push fluid flow through the ventricular system to the subarachnoid space.

Under steady state conditions, the choroid plexus is under considerable sympathetic inhibitory tone, which causes a reduction in the net rate of CSF production. Electrical stimulation may be used to induce a nerve block or sympathetic inhibition at the superior cervical ganglia causing an increase in CSF formation and thereby enhancing glymphatic clearance. Various electrical stimulation therapies may be used to cause sympathetic inhibition and inhibit central sympathetic pathways to increase CSF production, for example, autonomic nerve stimulation or focused ultrasound stimulation of the vagus nerve, aortic depressor nerve, and carotid sinus nerve may be used.

2. Dilating and/or Modulating Pulsatility of Penetrating Arterial Vessels into the Brain Glymphatic transport of the CSF is also driven by cerebral arterial pulsation, driving the CSF along the periarterial spaces.

Electrical stimulation may be used to dilate arterial vessels and increase the pulsatility/pulsation of penetrating arterial vessels in the brain. Various electrical stimulation therapies may be used to cause dilation of arteries, for example, stimulation of the trigeminal nerve, facial nerve, vagus nerve, carotid sinus nerve, and/or aortic depressor nerve may be used. Direct stimulation therapies, for example, direct cortical stimulation, deep brain stimulation, transcranial direct current stimulation, transcranial magnetic stimulation, etc., may also be used to stimulate local areas of brain tissues. Moreover, electrical stimulation of these nerves or local areas in a temporal pattern, i.e., interpulse intervals that do not vary as a function of time, may selectively cause oscillations in pressure and dilation of arteries that also improves glymphatic clearance.

3. Increasing Permeability of AQP4 Water Channels Expressed in Astrocytic Endfeet that Ensheathe the Brain Vasculature AQP4 water channels are essential for transporting water in and out of the brain parenchyma by enhancing transmembrane water flux in astrocytes and is a major clearance pathway of ISF solutes from the brain's parenchyma.

Electrical stimulation may be used to increase the permeability of AQP4 water channels. Various electrical stimulation therapies may be used to increase the permeability of AQP4, for example, tDCS, cortical stimulation, focused ultrasound stimulation, and DBS used to stimulate the cortex of the brain.

4. Decreasing Intracellular Fluid Volume/Increasing the Distance Between Neuronal/Non-Neuronal Cells Therefore Decreasing the Resistance of CSF Penetration in the ISF Space Increases in interstitial space volume reduce tissue resistance towards convective flow thus permitting CSF-ISF exchange.

Electrical stimulation may be used to decrease the resistance to CSF flow through the increase in interstitial space volume. Various electrical stimulation techniques may be used to decrease neural activity, which is shown to cause neurons to shrink and expel fluid contents into the ISF due to the decreased metabolic demand, thereby decreasing the intracellular fluid volumes and increasing the distance between neurons. This creates larger effective distances between cells allowing ISF to flow more freely between cells and decreasing the resistance to CSF flow.

For example, vagal nerve stimulation and transcranial magnetic stimulation may be used to suppress neural activity in areas of the brain. Moreover, modulating the temporal pattern, i.e., interpulse intervals that do not vary as a function of time, of the electrical stimulation may optimize the interstitial space volume necessary for convective movement and clearance of misfolded proteins.

Vagal nerve stimulation may also be used to modulate levels of norepinephrine in locus coeruleus (LC), the principal site for norepinephrine release in the brain. Vagal nerve stimulation may be used to increase norepinephrine levels and decrease neural activity, causing neurons to shrink and expel their fluid contents into the extracellular volume and increase the interstitial volume.

5. Inducing Slow Wave Oscillations in Specific Brain Areas that are the Hallmark of REM Sleep During sleep, the extracellular space expands and contracts to improve glymphatic clearance. During slow wave oscillations, ISF volume increases to remove waste products in a slow-moving stream of extracellular fluid, which have been linked to improved glymphatic clearance during sleep.

Electrical stimulation may be used to induce slow wave oscillations. Electrical stimulation may be used to activate cholinergic neurons in the pedunculopontine tegmentum and laterodorsal tegmentum during non-REM sleep to increase the number of slow wave REM episodes as determined by EEG (theta 5-9 Hz). Similarly, local tonic activation of the thalamic reticular nucleus may be used to induce slow wave activity in a spatially restricted region of the cortex and electrical stimulation of globus pallidus externa may be used to induce both REM and non-REM sleep.

6. Directly Attracting Proteins to an Electrode Via Application of a Stimulus Waveform During electrical stimulation, charged proteins can accumulate on the surfaces of electrodes of opposite charge.

A non-invasive electrode system such as transcranial direct current stimulation, or an invasive electrode system such as an intravascularly placed electrode or an implanted electrode may be used to draw charged proteins, such as amyloid beta, towards the stimulated electrode and toward venous return, thus enhancing the clearance of misfolded proteins. For example, an electrode system may be implanted in a vein while biphasic pulses may be used to draw the charged proteins to the electrode system.

While normally the accumulation of proteins can impede the flow of fluids at those locations, circumferential electrode placement may prevent such blockages.

The clearance of pathogenic proteins from the CNS may be evaluated by any appropriate method. For example, the clearance of pathogenic proteins from the CNS may be evaluated by measuring neural activity in the CNS and/or the PNS. In certain instances, a course of treatment and the severity of one or more symptoms related to the proteinopathy (e.g., a neurodegenerative disease) being treated may be monitored. Any appropriate method may be used to determine whether or not the severity of a symptom is reduced. For example, the severity of a proteinopathy (e.g., a neurodegenerative disease) may be assessed using neuroimaging techniques (e.g., computerized topography (CT) scan, diffuse optical imaging (DOI), event-related optical signal (EROS), magnetic resonance imaging (MRI), magnetoencephalography (MEG), positron emission tomography (PET), single-photon emission computed tomography (SPECT), and cranial ultrasound), cognitive function testing (e.g., learning tests and memory tests), motor function testing, sensory function testing, CSF testing, blood testing, and/or genetic testing at different time points. Real time monitoring of neural activity in the CNS and/or the PNS may teach the patient to self-administer the stimulation to maximize target engagement and/or treatment effectiveness, e.g., by adjusting stimulation voltage, pulse rate, frequency, duration. Multiple feedback mechanisms may also be utilized to teach the patient to self-administer the electrode configuration to maximize target engagement and/or treatment effectiveness.

The invention will be further described in the following examples, which do not limit the scope of the invention described in the claims.

Example 1: Functional Magnetic Resonance Imaging (fMRI) Blood Oxygen Level-Dependent (BOLD) Effects in the Swine Following Vagus Nerve Stimulation The vagus nerve was stimulated in three large swine under the following conditions: 4 V, 75 Hz, 200 μsec pulse width, 6 sec, n=3. Functional magnetic resonance imaging (fMRI) was used to measure changes in blood oxygen level dependent (BOLD) effects in the brain before and after electrical stimulation in multiple brain structures (e.g., nucleus accumbens, insula, prefrontal cortex, cerebellum). The BOLD response was used as an indicator of hemodynamic response and a marker of neural activity in the brain.

Figure 1B:
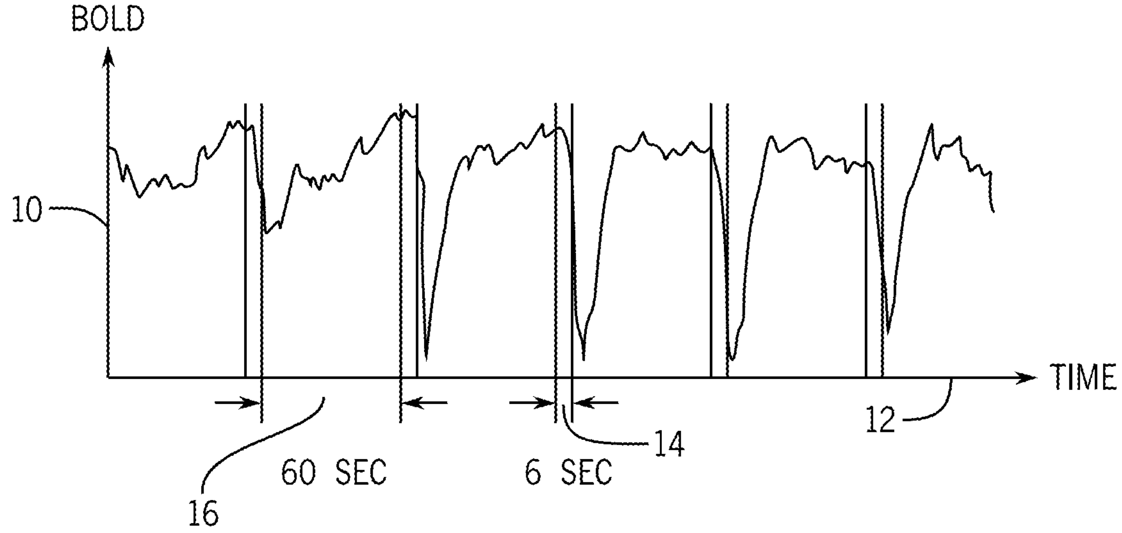

Referring to FIGS. 1A and 1B, the BOLD response (shown on the y-axis 10) is shown over time (shown on the x-axis 12) with electrical stimulation periods 14 of six seconds being administered with sixty second rest periods 16 in between and then repeated five times. As shown in FIG. 1A, the stimulation was found to produce a positive BOLD response demonstrating increased neural activity in some areas of the brain (e.g., nucleus accumbens and cerebellum), and when administered in a temporal pattern (e.g., six seconds stimulation followed by sixty seconds rest and repeated five times) produces a positive BOLD response followed by a negative BOLD response to affect arterial pulsatility. As shown in FIG. 1B, the stimulation was found to produce negative BOLD response demonstrating decreased neural activity in other areas of the brain (e.g., prefrontal cortex and insula), and when administered in a temporal pattern (e.g., six seconds stimulation followed by sixty seconds rest repeated five times) produces a negative BOLD response followed by positive BOLD response to similarly affect arterial pulsatility. The results demonstrate that electrical stimulation to the vagus nerve may be used to both modulate (increase and decrease) the hemodynamic response as well as modulate (increase and decrease) neural activity in multiple brain structures.

Example 2: Electrode Subjected to Electrical Stimulation In-Vitro within the Normal Parameters of Neuromodulation Therapy An electrode was subjected to electrical stimulation in-vitro in phosphate buffered saline with bovine serum albumin (protein concentration standard) added. Electrical stimulation was performed under the following conditions within the standard parameters of electrical stimulation therapies: 10 mA, 500 microsecond pulse width, 100 Hz.

It was found that the electrical stimulation selectively attracted charged proteins to the electrodes in comparison to unstimulated controls. Bovine serum albumin was shown to aggregate on the stimulated electrode while unstimulated electrodes showed no aggregation of misfolded proteins.

Example 3: Electrical Stimulation of the V1 Branch of the Trigeminal Nerve to Enhance Glymphatic Clearance Referring to FIG. 2, stimulating the trigeminal nerve 18 to enhance glymphatic clearance in human patients 20 may be implemented as described below.

The present invention may be utilized to treat patients 20 suffering from a number of proteinopathies such as Alzheimer's disease and Parkinson's disease, and in patients 20 where trauma to the brain causes a deficit in clearance of metabolites and misfolded proteins that lead to secondary damage or impairs learning/memory (e.g., traumatic brain injury, stroke, etc.). The system may also be used to prophylactically treat patients 20 deemed at risk for proteinopathies due to high blood pressure, genetic screening, etc. Finally, the system may be used to treat patients 20 with depression, anxiety and epilepsy by increasing the influx of CSF into the ISF and thereby decreasing distance between nerve cells and reducing ephaptic coupling.

Electrical stimulation may be applied to the V1 branch of the trigeminal nerve 18. The supraorbital branches of the trigeminal nerve 18 extend from the eye socket across the forehead 22 proximate the skin. Non-invasive electrodes 24 may be placed on the skin above the supraorbital braches of the trigeminal nerve 18 and electrical current delivered to the electrodes 24 to activate the trigeminal nerve 18 or trigeminal nerve fibers.

Trigeminal nerve 18 stimulation increases glymphatic clearance through three separate and distinct physiological mechanisms previously discussed above. It is understood that different patients 20 may receive varying amounts of benefit based on the optimization of stimulus parameters for a particular physiological mechanism.

The first physiological mechanism by which trigeminal nerve 18 stimulation may enhance glymphatic clearance is by entrainment at gamma (30-90 Hz) or theta (4-12 Hz) rhythms typically generated through visual stimuli and transcranial magnetic stimulation, respectively. Unlike the presentation of a flashing visual field or transcranial magnetic stimulation which makes very loud noises during operation and requires an expensive, large system, trigeminal nerve 18 stimulation may be administered via a non-invasive adhesive bandage 26 with electrode 24 contacts placed over the right and left supraorbital branches during sleep.

A second physiological mechanism by which trigeminal nerve 18 stimulation may enhance glymphatic clearance is by dilating the cerebral/pial arteries and other major vessels in the brain. Dilation of these arteries causes the vessel to displace CSF in the Virchow-Robin space surrounding the vessel, forcing CSF into the ISF through AQP4 channels, enhancing glymphatic flow and therefore clearance. Trigeminal/facial nerve stimulation dilates the cerebral arteries and descending vessels. The autonomic pathways may be stimulated intermittently to deliberately cause the dilation and then constriction of these vessels to introduce pulsatility to enhance CSF penetration into the ISF.

The third physiological mechanism by which trigeminal nerve 19 stimulation may enhance glymphatic clearance is by reducing cortical excitability. Norepinephrine antagonists or other pharmacological treatments to decrease the activity of neurons causes the neurons to shrink and expel their fluid contents into the extracellular volume. This in turn causes an increase in ISF volume, expanding the distance between cells that obstructing glymphatic flow, thereby decreasing the resistance to glymphatic flow. Methods that reduce neural excitability enhance glymphatic clearance by increasing glymphatic flow.

Figure 2:
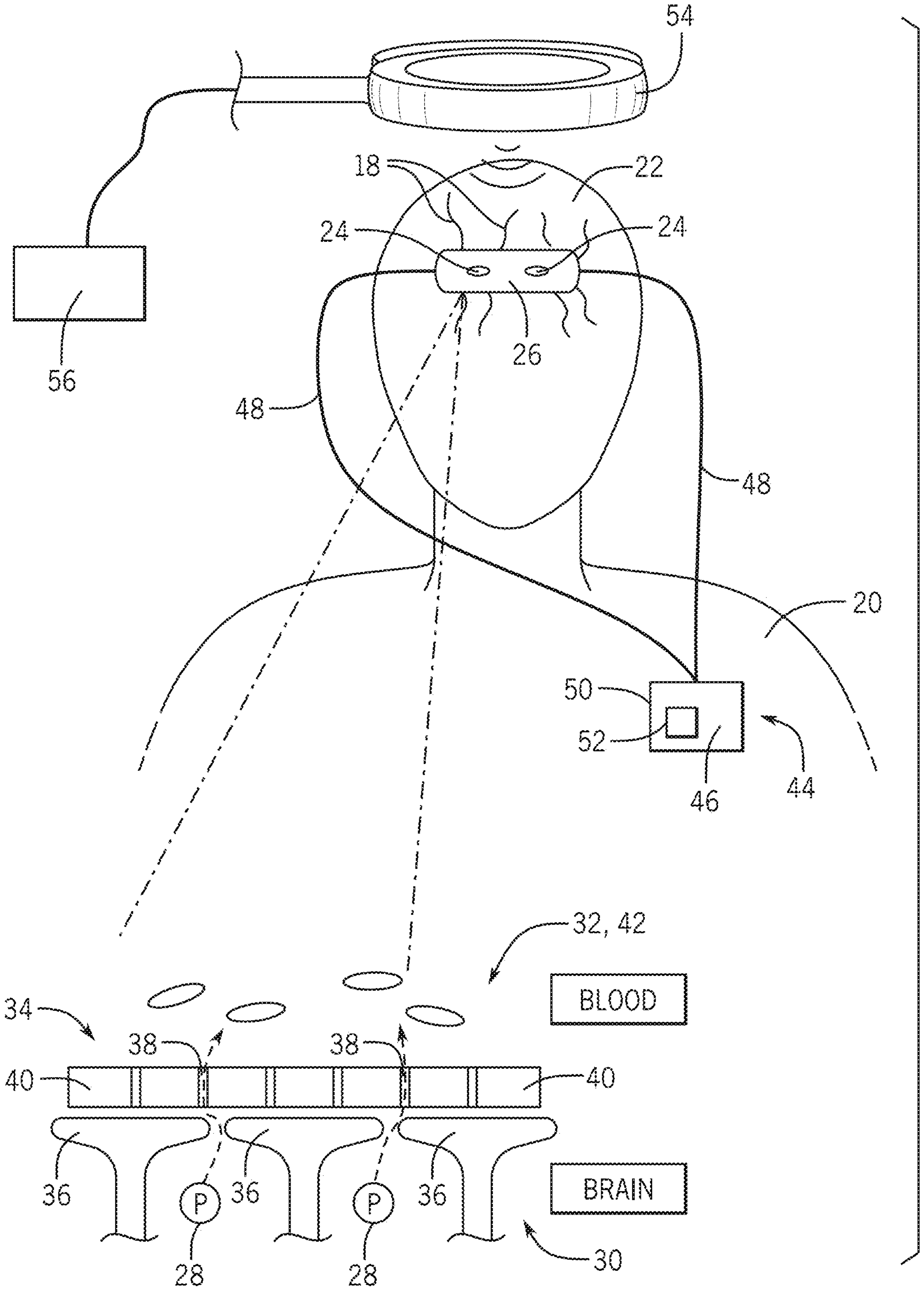
FIG. 2 is a schematic of an electrostimulation device being applied to a patient, specifically, transcranial direct current stimulation (tDCS) and transcranial magnetic stimulation (TMS), and an enlarged inset view of proteins passing the blood-brain barrier in the brain as a result.

Referring to the inset of FIG. 2, these physiological mechanisms work together to increase the outward flow of misfolded proteins and other waste materials 28 from the brain 30 to the blood 32 through the blood-brain barrier 34 composed of astrocytic endfeet 36 that ensheathe the brain 30 vasculature and tight junctions 38 between endothelial cells 40 around the capillaries 42.

In one embodiment of the present invention, a pulse generator system 44 may include electrodes 24 that are placed over the supraorbital branch of the trigeminal nerve 18 using multiple electrodes 24 placed on a mildly adhesive strip 26 on the patient's forehead 22. In one embodiment one electrode 24 is placed over a single supraorbital branch on one side of the head, with a large return electrode placed on the surface of the skin at a comfortable distance from the trigeminal (monopolar/unipolar configuration). In one embodiment, and as shown in FIG. 2, two or more electrodes 24 are placed over both the right and left supraorbital branch of the trigeminal nerve 18, and combinations of electrodes 24 (bipolar and tripolar configurations, changes in electrode orientation to maximize activation) are used to optimize target engagement without inducing unwanted side effects (direct muscle activation, pain/irritation).

The electrodes 24 are connected to an external pulse generator 46 via a conducting wire 48, which provides the energy for stimulation. The external pulse generator 46 may provide a lightweight wearable housing 50 having a battery 52 that may be clipped onto the patient's clothing or adhered to the patient's body and worn underneath clothing. The external pulse generator 46 may be worn by the patient 20 outside of the hospital environment, for example, at home or during normal everyday activities. Therapy may be administered during sleep (for example, continuously for at least four hours, six hours, or eight hours), or may be used throughout the day at various intervals as convenient for the patient 20. The therapy may be used over the span of several days, weeks, or months as needed.

The external pulse generator is capable of delivering stimulating pulses with pulse amplitudes up to 60 Volts/60 mAs, pulse widths from 15 microseconds to 10000 microseconds, and pulse frequencies ranging from 0.1 Hz to 50 kHz. The extended voltage range may be high enough to ensure stimulation to the nerve at a desired depth from the surface of the skin. The pulse width range allows flexibility in determining chronaxie to separate intended effects from unwanted side effects, as well as including the possibility of delivering 5 kHz sinusoids for intermittent bursts of up to 100 microseconds in duration. Although it is anticipated that therapeutic frequency ranges will typically be under 50 Hz, an extended range out to 10 kHz may be desirable to enable high-frequency block of nerves responsible for side effect. In some cases, a high frequency carrier wave (nominal 5 kHz) may be utilized intermittently at a lower frequency (nominal 40 Hz) to help penetrate through muscle and stimulate the trigeminal nerve 18 and/or in brain areas where corresponding evoked activity is expected.

Nominal stimulation parameters intended to entrain the trigeminal nerve 18 at beta/gamma (12-100 Hz) or theta frequencies (4-8 Hz) may be 24 Volts at 1000 microsecond pulse widths (physiological mechanism 1). Nominal stimulation parameters intended to dilate the cerebral/pial and/or penetrating arteries may be 280 microsecond pulse width cathodic-leading biphasic pulses at 10 Hz and 24 Volts (physiological mechanism 2). Temporal patterning (turning on/off to cause oscillating dilation/constriction of the vessel) at a nominal frequency of 0.2 Hz of the electrical stimulus may be introduced to induced pulsatility. Nominal stimulation parameters intended to reduce cortical activity are 24 Volts, 333 Hz, at 0.5 msec pulsewidths (physiological mechanism 3).

Therapeutic parameters may be optimized for each of the physiological mechanisms outlined above, which may provide the desired trade-off between therapeutic effect and therapy limiting side effects (e.g., induced muscle twitching, pain, irritation). It is anticipated that the patient 20 will be trained to slowly increase the current amplitude of stimulation until just before perceptible side effects to maximize therapeutic effects. In order to prevent irreversible electrochemical reactions and maximize target engagement with the trigeminal nerve 18, in one embodiment, the operating mode is a Lily biphasic, cathodic leading pulse. In other embodiments, anodic leading pulses and asymmetrical pulses may also be utilized to increase tolerable dose without side effects. In other embodiments, a sinusoid pulse may be used. Constant current pulses may be used such that the charge density delivered will not change as a function of impedance changes at the electrode interface, but constant voltage pulses may also be utilized in some embodiments to limit the complexity of the pulse generator system 44.

Multiple feedback mechanisms may be utilized to teach the patient 20 to self-administer the electrode configuration to maximize target engagement with the trigeminal nerve 18 and/or maximize glymphatic clearance. In one embodiment, the clearance of gadolinium contrast is used in conjunction with magnetic resonance imaging (MRI) as a surrogate for the movement of misfolded proteins. In another embodiment, imaging modalities such as MRI/SPECT/PET are used to demonstrate evoked trigeminal nerve 18 activity is being transmitted to the brain (single photon emission computed tomography {SPECT}, position emission tomography {PET}). Alternatively, recording electrodes or other sensing modalities such as optical coherence tomography (OCT) may be used to record and optimize evoked neural activity at the trigeminal nerve 18 and/or in brain areas where corresponding evoked activity is expected.

Unlike visual, auditory, and haptic stimuli which will induce neural activity only in the small region of sensory cortex associated with those sensory inputs—and therefore only enhance glymphatic clearance in these areas—the V1 branch of the trigeminal nerve 18 projects to the nucleus tractus solitaries (NTS), the locus coeruleus, reticular formation, raphe nuclei and thalamic structures, and thereafter other sensory, limbic, and other cortical and subcortical structures affecting more areas. Also unlike visual, auditory, or haptic stimulus, electrical stimulation of the V1 branch of the trigeminal nerve 18 does not override existing sensory pathways that are necessary for normal function (e.g., vision, hearing, touch). Rather, invasive or non-invasive electrical stimulation of the V1 branch of the trigeminal nerve 18 may be utilized during sleep and, for example, continuously for more than 8 hours.

Example 4: Transcranial Magnetic Stimulation of the Central Nervous System to Enhance Glymphatic Clearance Referring again to FIG. 2, an alternative embodiment of the present invention is shown. In this embodiment, TMS may be used to enhance glymphatic clearance in human patients 20. A magnetic field generator or coil 54 is placed near the head of the patient 20. The coil 54 is connected to a pulse generator 56 that delivers electric current to the coil 54. The electric current delivered to the coil 54 produces an electric current to the brain of the patient 20 below the coil 54 via electromagnetic induction to stimulate the desired nerve or area of the brain, for example the CNS of the patient 20.

In a similar manner as described above in Example 3, TMS may affect various physiological mechanisms known to enhance glymphatic clearance in the brain.

Figure 3:
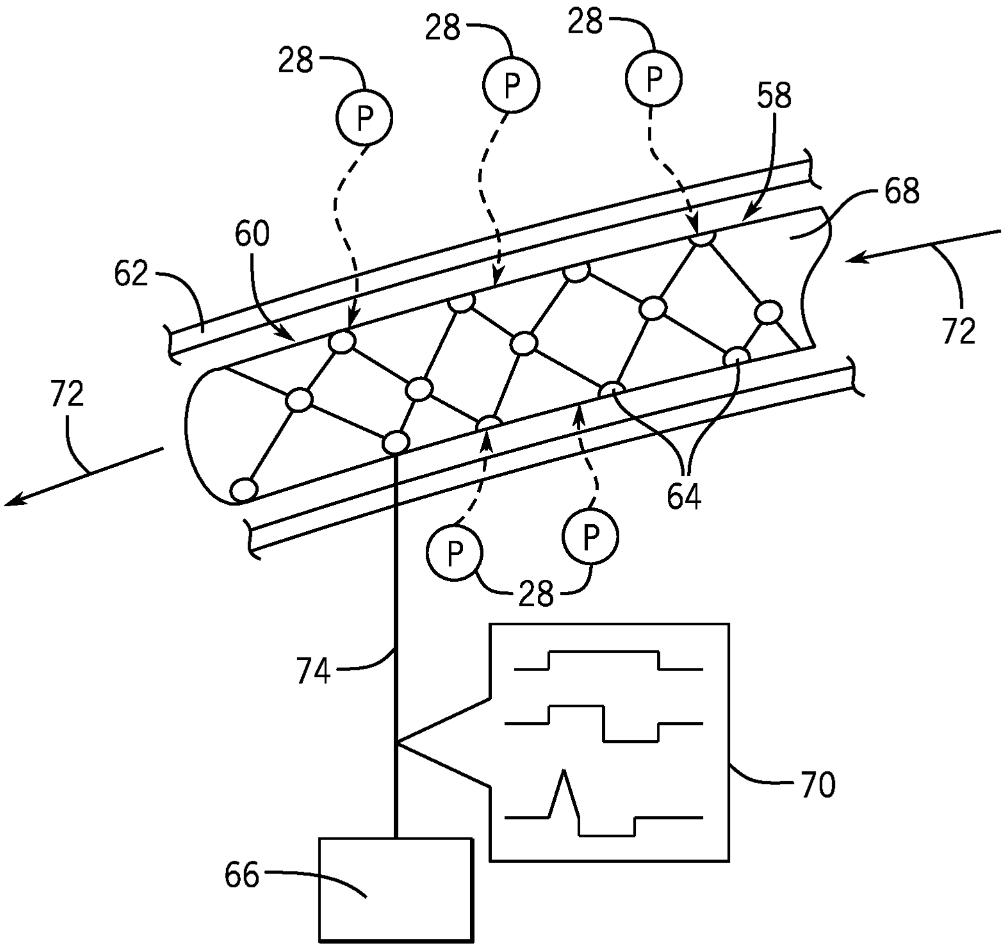
FIG. 3 is a schematic of a venous stent with electrodes placed intravenously within a patient and electrical pulses being provided to the stent to draw proteins to the electrodes.

Example 5: Electrical Stimulation from a Venous Stent Placed within the Sagittal Sinus Vein Referring to FIG. 3, drawing misfolded proteins towards intravenous electrodes and venous return to enhance glymphatic clearance in human patients 20 may be implemented as described below.

A vascular stent 58 may be implanted within the lumen 60 of a patient's blood vessel 62. The vascular stent 58 has a tubular construction which includes external electrodes 64 surrounding an inner layer of insulation 68. The external electrodes 64 are connected to an implantable pulse generator (IPG) 66 providing a pulse 70 (e.g., monophasic, symmetrical biphasic, non-symmetrical biphasic) to direct current outward toward the inner walls of the blood vessel 62.

The external electrodes 64 may be placed externally to the inner layer of insulation 68 to prevent aggregation of charged proteins 28 in the blood flow path through the stent 58 and preventing blood flow through the blood vessel 62 as shown by arrow 72.

In one embodiment of the present invention, the patient 20 will be assessed by anesthesia for suitability to undergo general anesthesia. Enteric-coat acetylsalisylic acid 81 mg daily and clopidogrel 75 mg daily will be prescribed for five days before the stent placement procedure. Patients 20 with a history of thrombophilia will be anticoagulated before the procedure and receive single agenet antiplatelet therapy. The procedure is to be performed under general anesthesia with systemic anticoagulation using intravenous heparin administered to maintain an activated clotting time of more than twice the normal level.

Femoral access is to be obtained and a guide catheter positioned into the right or left jugular bulb of the patient 20. A high-flow microcatheter is then navigated into the superior sagittal sinus with the support of a microwire. Venography will be performed by selective contrast injections through the microcatheter to aid in visualization of placement of the stent 58. The IPG 66 may provide stimulus energy and may be placed in the chest of the patient 20, with a lead wire 74 connecting the stent electrodes 64 to the IPG 66 held within the vein 62 traversing and exiting through the subclavian before connection to the IPG 66.

Maximizing clearance of proteins is accomplished by stimulating the electrodes 64 using constant-current, charged-balance, cathodic-leading, biphasic pulses 70 to safely generate a small DC bias on the electrodes 64. Charge density will be limited to 50 micro Coulombs/cm2 to prevent unwanted electrochemical reactions. Nominal stimulation parameters are 100 Hz, 500 microsecond pulse width, and 10 mA, although the current amplitude may be adjusted for the maximum tolerable level of the patient 20.

The stimulated electrodes 64 will attract charged proteins within the local vicinity of the electrode 64 to be cleared via para-venous efflux. Increasing the clearance within the local vicinity of the electrode 64 in turn creates an osmotic gradient to enhance convective clearance of misfolded proteins at a distance from the electrode 64.

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art may also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. When elements are indicated to be electrically connected, that connection may be direct or through an intervening conductive element.

When introducing elements or features of the present disclosure and the exemplary embodiments, the articles "a", "an", "the" and "the" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An apparatus for promoting cerebral spinal fluid (CSF) clearance comprising:

a stimulation device selected from the group consisting of apparatus for peripheral nerve stimulation, transcranial direct current stimulation (tDCS), deep brain stimulation (DBS), cortical stimulation, spinal cord stimulation (SCS), transcranial magnetic stimulation (TMS), focused ultrasound, infrared stimulation, and optical stimulation, the stimulation device for promoting clearance and positionable to communicate with at least one of the cranial nerve and cortical region of the brain;

a pulse generator communicating with the stimulator to generate a stimulating signal to stimulate at least one of a cranial nerve and a cortical region of the brain;

a sensor providing a flow signal indicating CSF flow;

wherein the pulse generator receives the flow signal to provide closed-loop control of the stimulating signal between first and second periods dilating and constricting cerebral vessels of the at least one cranial nerve and cortical region of the brain according to the flow signal indicating CSF flow to control outflow of the CSF.

2. The apparatus of claim 1, wherein the stimulating signal is at least one of peripheral nerve stimulation, transcranial direct current stimulation (tDCS), deep brain stimulation (DBS), cortical stimulation, spinal cord stimulation (SCS), transcranial magnetic stimulation (TMS), focused ultrasound, infrared stimulation, and optical stimulation.

3. The apparatus of claim 1, wherein the stimulating signal has a frequency matching at least one of Beta wave frequencies, Gamma wave frequencies, and Theta wave frequencies.

4. The apparatus of claim 1, wherein the closed loop control of the stimulating signal is selected to induce sympathetic inhibition.

5. The apparatus of claim 1, wherein the closed loop control of the stimulating signal is selected to modulate at least one of adenosine, epinephrine, and norepinephrine release.

6. The apparatus of claim 1, wherein the flow signal adjusts at least one of the stimulating signal frequency and duration of the first and second periods.

7. The apparatus of claim 6, wherein the pulse generator adjusts the stimulating signal frequency and the duration of the first and second period in the closed-loop control.

8. The apparatus of claim 1, wherein the sensor measures an electrophysiological measurement in providing the flow signal.

9. A method for promoting cerebral spinal fluid (CSF) clearance comprising:

(a) stimulating at least one of a cranial nerve and a cortical region of the brain with a stimulating signal;

(b) sensing CSF flow;

(c) implementing closed-loop control of CSF flow by closed loop control of the stimulating signal between first and second periods dilating and constricting cerebral arteries of the at least one cranial nerve and cortical region of the brain according to the sensed CSF flow to control outflow of the CSF.

10. The method of claim 9 wherein the stimulating signal has a frequency matching at least one of Beta wave frequencies, Gamma wave frequencies, and Theta wave frequencies.

11. The method of claim 9, wherein the stimulating signal is closed-loop controlled to induce sympathetic inhibition.

12. The method of claim 9, wherein the stimulating signal is closed-loop controlled to control at least one of adenosine, epinephrine, and norepinephrine release.

13. The method of claim 9, wherein the sensed CSF flow adjusts at least one of the stimulating signal frequency and duration of the first and second periods.

14. The method of claim 13, wherein a frequency of the stimulating signal and the duration of the first and second period are adjusted automatically according to the sensed CSF flow to control the outflow of CSF.

15. The method of claim 9, wherein the sensed CSF flow is derived from an electrophysiological measurement.

* * * * *